United States Patent [19]
Ackermann et al.

[11] 4,327,230
[45] Apr. 27, 1982

[54] METHOD FOR THE CONTINUOUS PREPARATION OF ALCOHOLATES

[75] Inventors: Otto Ackermann; Hans Leuck; Günther Meyer, all of Troisdorf-Sieglar; Gerhard Schmeling, Brühl, all of Fed. Rep. of Germany

[73] Assignee: Dynamit Nobel AG, Troisdorf, Fed. Rep. of Germany

[21] Appl. No.: 128,421

[22] Filed: Mar. 10, 1980

Related U.S. Application Data

[63] Continuation of Ser. No. 913,416, Jun. 7, 1978, abandoned.

[30] Foreign Application Priority Data

Jun. 11, 1977 [DE] Fed. Rep. of Germany ....... 2726491

[51] Int. Cl.³ .............. C07C 29/70; C07C 35/04; C07C 35/06; C07C 35/08
[52] U.S. Cl. .................. 568/851; 568/700; 568/835; 568/838; 568/839
[58] Field of Search ............... 568/851, 700, 839, 838, 568/835

[56] References Cited

U.S. PATENT DOCUMENTS

| | | |
|---|---|---|
| 2,081,322 | 5/1937 | Carney . |
| 3,028,221 | 4/1962 | Schechter et al. . |
| 3,418,383 | 12/1968 | Lenz et al. .......................... 568/851 |

FOREIGN PATENT DOCUMENTS 490388 8/1937 United Kingdom ................ 568/851

Primary Examiner—Joseph E. Evans
Attorney, Agent, or Firm—Sprung, Felfe, Horn, Lynch & Kramer

[57] ABSTRACT

A process for the continuous production of an alkali metal alcoholate of a higher alcohol which comprises continuously introducing a higher alcohol into a reaction vessel, continuously introducing an alkali metal alcoholate of a lower alcohol into said reaction vessel and continuously and simultaneously distilling over and removing from said reaction vessel lower alcohol which forms.

17 Claims, 1 Drawing Figure

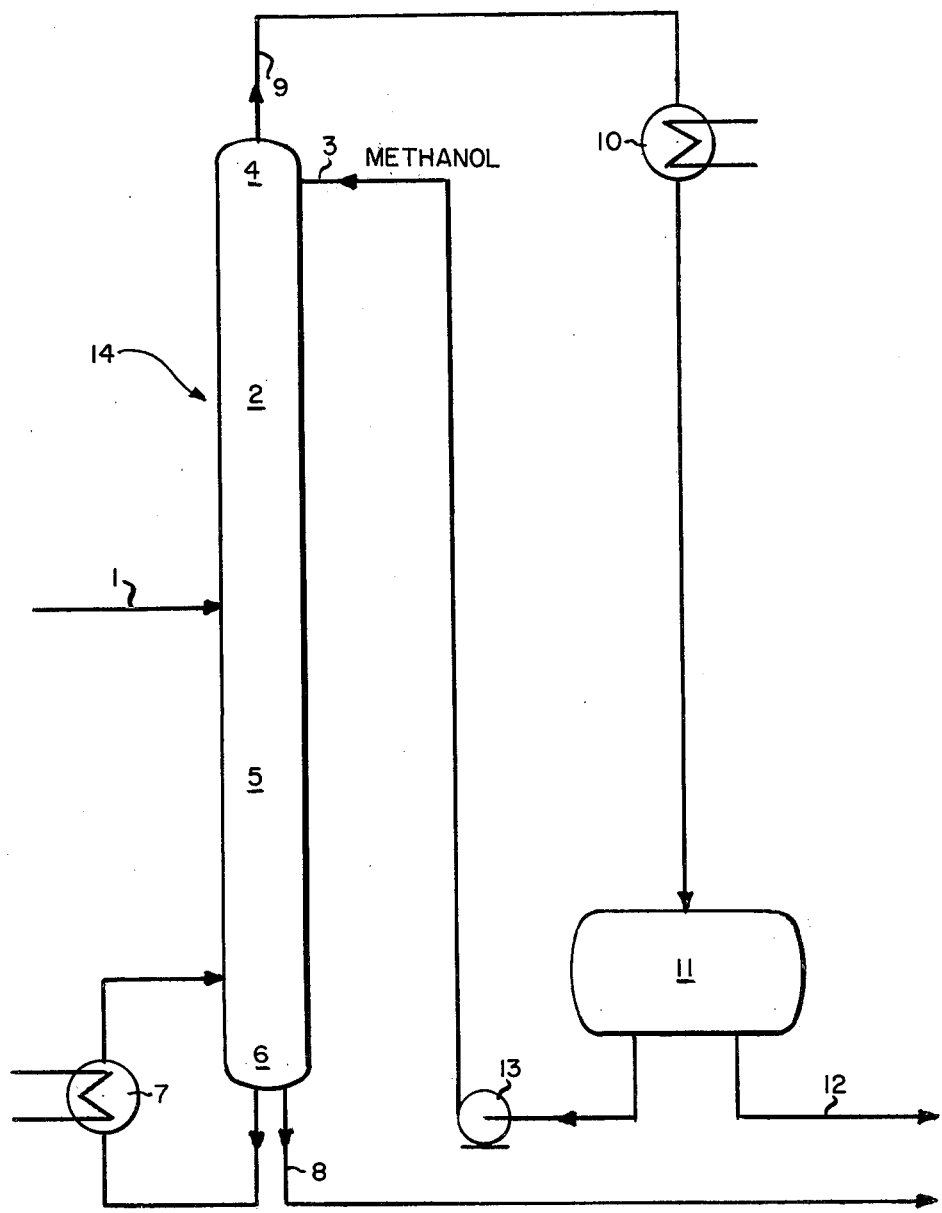

METHOD FOR THE CONTINUOUS PREPARATION OF ALCOHOLATES

This is a continuation of application Ser. No. 913,416, filed June 7, 1978, now abandoned.

BACKGROUND OF THE INVENTION

1. Field of the Invention

The subject matter of the invention is a method for the continuous preparation of alkali alcoholates by the transalcoholization of alkali alcoholates of lower alcohols, especially of methanol or ethanol, with higher alcohols provided in excess, especially aliphatic or cycloaliphatic univalent alcohols, and the removal of the lower-boiling alcohol.

2. Discussion of the Prior Art

It is known to prepare sodium methylate by passing an aqueous, preferably 50 weight-percent sodium hydroxide solution countercurrently to methanol vapor thereby causing them to react. This method, however, is very complex, especially when it is used in the preparation of alkali alcoholates which are derived from alcohols of 2 or more carbon atoms. In order to obtain sufficiently pure alcoholates and a high transformation, the alcohol that is charged must be substantially anhydrous. 77 to 84% of the alcohol input passes out through the top of the reactor and contains all of the water. The separation of this mixture into alcohol for recycling to the reaction and into alcoholfree water to comply with environmental protection requirements is very costly in terms of apparatus and energy.

It is also known to prepare alkali metal alcoholate by reacting 100% sodium methylate with the alcohol of the desired alcoholate in a stirring tank, the methanol that forms being removed from the system. Since this reaction is a pure equilibrium reaction of the general formula:

$$MeOR + R'OH \rightleftharpoons MeOR' + ROH$$

Me = alkali metal
R = lower alcohol
R' = higher alcohol

It becomes very difficult to prepare high-purity alkali metal alcoholates while achieving a high alkali metal methylate transformation because of the need for a thorough removal from the system of the methanol that forms. Moreover, the separation of the alcohol mixture taken from the stirrer-equipped reactor is expensive in terms of technology and energy.

In another known process (DT-PS No. 12 54 612), a solution of sodium methylate in excess amounts of a transalcoholization alcohol is fed countercurrently to the vaporized transalcoholization alcohol in a column. The desired new alcoholate solution is withdrawn at the bottom, and the methanol that forms is removed with the excess amount of transalcoholization alcohol at the top and this mixture is separated in a second column. For the achievement of an extensive sodium methylate teransformation, a relatively great amount of transalcoholization vapor is used for the purpose of removing the methanol from the equilibrium. This, too, requires a great amount of energy both for the performance of the transalcoholization itself and for the subsequent separation of the methanol and transalcoholization alcohol. This greatly detracts from the enconomy of the process. Furthermore, the amount of apparatus and hence the investment cost required for the production of a pure alcoholate is likewise great.

Also, the adjustment and the maintenance of a constant concentration of the alcoholate in the reaction product, which is specific in each individual case, is difficult. By means of the heating system provided in the bottom of the column, this concentration is adjusted in relation to the solubility behavior of the end product, to the quantity and the temperature of the higher alcohol vapor fed to the bottom of the column, and to the amount of vapor withdrawn at the top of the column. Even slight uncontrolled differences in the heat input produce fluctuations of the concentration, which can give rise to trouble. If the alcoholate concentration in the alcoholate solution being removed is too high, there is the danger that, even in the event of a slight temperature increase in the jacket-heated pipelines through which the solution of the alcoholate of the higher alcohol is taken from the column, an evaporation of alcohol can occur. This can result in a pecipitation of solid matter. A slight lowering of the temperature in the heated pipelines can also cause a precipitation of solid matter when the alcoholate concentration is too high, and this can cause great trouble by clogging the lines.

Too low an alcoholate concentration in the end product, on the other hand, necessitates a greater investment in apparatus for the subsequent concentration of the solution to refine the alkali alcoholate or to prepare concentrated solutions of the alkali alcoholate in the higher alcohol.

SUMMARY OF THE INVENTION

It is an object of the present invention to provide a method for the preparation of alkali alcoholates of higher alcohols by the transalcoholization of alkali alcohols, of lower alcohols, in which high end-product purities in relation to the input components are achieved in a most convenient manner, along with specifically prescribed concentrations of the higher alcoholate in the transalcoholization alcohol.

Broadly the invention contemplates a process for the continuous production of an alkali metal alcoholate of a higher alcohol which comprises continuously introducing a higher alcohol into a reaction vessel, continuously introducing an alkali metal alcoholate of a lower alcohol into said reaction vessel and continuously and simultaneously distilling over and removing from said reaction vessel lower alcohol which forms.

Thus, the problems of prior art processes are solved in accordance with the invention in that the transalcoholization and the refinement by distillation of the lower alcohol are performed simultaneously such as in an arrangement having a reaction section and a booster section (rectifying section) directly coupled thereto. With the alcoholate, dissolved in the lower alcohol if desired, and the transalcoholization alcohol being fed together to the upper part of the reaction section of the apparatus of the invention, a high purity product is advantageously obtained both with respect to the alcoholate being produced and the lower alcohol being taken from the top booster section. This is achieved by combining the chemical reaction with the distillative separation and rectification of the lower alcohol that is formed or added, in an apparatus in which one part operates as a reaction section and the other part boosts the lower alcohol to the desired purity.

By the procedure of the invention one can conduct the reaction in such a way that the transalcoholization takes place without the specific excess amount of alcohol vapor prescribed in German PS No. 1,254,612, with a most extensive transformation of the lower alkali alcoholate, and such that the methanol that forms is obtained in high purity in virtually a single operation.

The process of the invention is characterized furthermore by the fact that uncontrolled changes of concentration in the end product no longer need to be feared, and instead depending upon the concentration of the alcoholate solution of the lower alcohol in the transalcoholization alcohol before the reaction, one can remove the end product continuously from the reaction section of the column in the desired constant concentration.

The process of the invention is furthermore distinguished from the process of German Pat. No. 1,254,612 in that one can advantageous charge the alcoholates being transalcoholized, not in solid form, but in solution in the lower alcohol. This results in an additional economic advantage, since inexpensive starting substances can be used because the alcoholates to be transalcoholized, e.g., sodium methylate or sodium ethylate, are produced in the conventional production processes in which the alkali metals are reacted with the lower alcohols in the form of solutions in the lower alcohols, preferably methanol or ethanol.

In an advantageous development of the invention, an additional oversupply of the higher transalcoholization alcohol, coordinated with the reactants, is brought about in the liquid phase of the reaction section by adjusting the rate of refluxing of the lower alcohol in the booster section. Inasmuch as the lower alcohol is present at the beginning of the reaction and is added constantly during the operation of the column, the desired steady equilibrium establishes itself very rapidly.

Basically, however, alkali alcoholate solutions can be used which contain only the higher alcohol and are free from lower alcohol.

The procedure can be, for example, that, for the adjustment of the reflux rate of the lower alcohol, the latter is fed to the top of the column as a starting reflux, the reaction section and the bottom of the column being filled with the higher alcohol. After the operating temperature is reached, the alkali alcoholate solution in the higher alcohol is then fed in. During the reaction, fresh lower alcohol continuously forms, so that, after the desired reflux rate is reached, it is essentially unnecessary to add lower alcohol continuously to the solutions of the alkali alcoholate in the higher alcohol which are continuously being fed into the reaction section of the column.

One can also, however, fill the entire column with the transalcoholization alcohol and use the latter at first also as the starting reflux. After the operating temperature is reached, the alkali alcoholate solution in the higher alcohol is charged. The steady operating state is reached when the reaction has then progressed to the point that as much lower alcohol has formed as is needed by the particular reactants for the reflux rate required in order to bring about the additional oversupply of the higher transalcoholization alcohol in the liquid phase in the reaction section.

The lower alcohol that continues to be formed afresh during the continuous operation is withdrawn from the top of the column and, if desired, removed from the system.

In addition to the initially mentioned, known means for shifting the equilibrium of the transalcoholization reaction by the separation of the lower alcohol, in the process of the invention, the internal rate of circulation of the transalcoholization alcohol in the reaction section is deliberately increased through the adjustment of the reflux rate of the lower alcohol in the booster section, and thus an oversupply of the higher transalcoholization alcohol is brought about in the liquid phase in the reaction section. The equilibrium shift, and consequently also the purity of the desired alcoholate, is thus additionally and advantageously influenced.

The boosted reflux of the invention thus brings about not only the known effect of an improved distillate purity in the reaction section, but also the important effect of an increased vapor-liquid loading in the reaction section by the higher alcohol and vice versa. The higher alcohol, as an ascending vapor, has the effect of driving the lower alcohol out of the reaction solution by lowering the partial pressure. It passes by condensation into the liquid phase in which the transalcoholization takes place and here, in an advantageous manner, produces the additional oversupply of the higher transalcoholization alcohol. The amount of transalcoholization alcohol which is evaporated in the reaction section is recondensable. This amount can be controlled by means of the lower alcohol reflux rate, is referred to as the internal circulation amount.

In this procedure there is also an important advantage over the known process of German PS No. 1,254,612, since the latter is performed without reflux. This means that in this process the rate of flow of the higher transalcoholization alcohol in the liquid phase in the reaction column is determined only by its percentage in the starting solution introduced into the column and by the amount of the lower alcohol being liberated in the reaction, for which a corresponding amount of the transalcoholization alcohol introduced in vapor form at the bottom of the column passes into the liquid phase in the substance exchange. The reaction in this case also takes place with an excess of the higher alcohol, but this is virtually determined by its excess in the starting solution.

In contrast, in the process of the invention, an additional excess of the higher alcohol is achieved in an exceedingly advantageous manner in the liquid phase in the reaction section, because, in contrast to the equilibrium reaction initially mentioned, a more or less great amount of the lower alcohol is fed back into the column.

At the top of booster amplifier part of the column, only a portion of the lower alcohol is removed in each case from the system, namely only the excess amount that is not needed for the adjustment of the reflux rate. The remainder of the lower alcohol returns to the booster section.

The lower alcohol carried off at the top is of high purity and can be reused without further distillation.

It has been found that the reflux rate to be established should be adapted to the transalcoholization alcohol that is used in each case. The reflux rate of the lower alcohol is between $>0$ and 200 moles preferably between 0.1 and 120 moles per mole of the input alkali alcoholates of the lower alcohol. In the production of alkali alcoholates of univalent alcohols, a reflux rate of up to 200 moles per mole of input alkali lower alcoholate is generally used. In the case of other alcohols, such as bivalent or polyvalent alcohols or in the case of those other than aliphatic or cycloaliphatic alcohols, the reflux rate can also be higher, if desired say up to 500 moles. The optimum reflux rate depends upon the particular alcohols involved and thus is best determined for a grain alcohol by preliminary experiment.

It is known, in the distillative separation of lower and higher alcohols in rectifying columns, to establish a reflux rate which is adapted to the desired purity of the distillate and to the particular column. The optimum reflux rate for this separation is, in a known manner, so established that, at an economical optimum with regard to the power to be expended for the separation of the lower and higher alcohol present in the system, an optimum is achieved with regard to the purity of the lower alcohol to be taken off at the top or of the higher alcohol to be withdrawn from the bottom, as the case may be.

In a preferred variant of the method of the invention, the reflux rate in the booster section, which is necessary for the advantageous control of the chemical reaction is made greater than the above-described optimum reflux rate which would be necessary for a pure separation in a rectifying column of the same separating power. In this manner the reaction equilibrium in the reaction part is shifted in favor of the desired alkali alcoholate.

If the transalcoholization alcohol is a primary univalent alcohol, it has been found desirable to adjust the reflux rate such that it amounts to up to 40 moles, preferably up to 12 moles, per mole of the alkali alcoholate of the lower alcohol charged, whereas the reflux rate in the case of secondary univalent alcohols amounts to up to 120 moles, preferably up to 50 moles. In the case of tertiary univalent alcohols, the reflux rate should be up to 200 moles, preferably up to 80 moles, per mole of the alkali alcoholate of the lower alcohol put in. Generally, speaking the reflux ratio is at least $>0$ preferably at least 0.4 moles per mole of alkali alcoholate charged.

The process of the invention can be performed either at standard pressure or at elevated or reduced pressure.

When the terms, "lower alcohols" or "higher alcohols," are used in the description of the invention, they refer in each case to the higher boiling or lower boiling alcohols. The reaction, of course, will succeed only when the transalcoholization alcohol has a higher boiling point than the alcohol of the starting alcoholate. The process of the invention is generally applicable to the reaction of alkali alcoholates of lower alcohols with higher alcohols, provided that the alcohols are distillable and the solubility characteristics of the starting alcoholates and preferably also of the end alcoholates permit reaction in the liquid phase.

The lower or higher alcohols, as the case may be, are not only univalent alcohols, but also, fundamentally, polyvalent alcohols, such as diols. Examples include ethylene glycol, diethylene glycol, the propanediols and the butanediols.

The method of the invention is, however, used preferably in the production of alkali alcoholates of univalent primary secondary or tertiary aliphatic or cycloaliphatic alcohols, preferably those of up to 18 carbon atoms, especially those of up to 12 carbon atoms.

Examples of reactable higher alcohols are the following: ethanol, n-propanol, n-butanol, 2-methylpropanol-(1), n-pentanol, 2-methylbutanol-(4), 2-methylbutanol-(1), 2,2-dimethylpropanol-(1), n-hexanol, 2-ethylhexanol-(1), lauryl alcohol, and stearyl alcohol. Examples of secondary higher alcohols are isopropanol, butanol-(2), pentanol-(2), pentanol (3), and 2-methylbutanol-(3). Examples of tertiary alcohols are 2-methylpropanol-(2), and 2-methylbutanol-(2). Cycloaliphatic alcohols are, for example, cyclopropanol, cyclobutanol, cyclopentanol, cyclohexanol, and alkyl-substituted derivatives thereof having a total of up to 18 carbon atoms, preferably up to 12 carbon atoms.

Preferred starting substances are alkali alcoholates of methanol or ethanol. Fundamentally, one can use as starting substances alkali metal alcoholates of higher alcohols of the above-named kind, in which case, of course, a still higher alcohol must be used as the transalcoholization alcohol.

The alkali of the alcoholate can be sodium, potassium and lithium, but it can also, of course, be cesium and rubidium. Sodium is preferred as the alkali.

For the continuous production of alkali metal alcoholates by transalcoholization, it is prefered to use an apparatus which is characterized by a column equipped with trays and having a lower reaction section for the liquid phase and an upper booster section.

Instead of perforated trays, bubble trays, valve trays or the like, packings in a suitable depth can, of course, also be used, as is the case in rectifying columns.

The column can consist of a plurality of individual vessels or columns connected in cascade, and they can preferably be disposed one over the other, or laterally offset from one another, but of course they can also be arranged said by side using appropriate pumps. In each case it must be assured by means of appropriate connecting lines and transport means, if any, that the reaction section and the booster section are coupled directly and that the reflux in the booster section can exercise an advantageous control on the chemical reaction taking place in the reaction section. Preferably a system is used in which the reaction section and the booster section are disposed on over the other in a single column.

BRIEF DESCRIPTION OF DRAWING

Referring to the attached drawing, the same is a flow diagram showing a specific embodiment of the invention.

DESCRIPTION OF SPECIFIC EMBODIMENT

Referring to the attached flow diagram, the reaction section 5 disposed below booster section 2 of column 14 is filled before start-up of the process with the higher alcohol. After the boiling temperature has been reached, the lower alcohol, methanol for example, is fed through line 3 to the top 4 of the column as the starter flux. At the same time the heat input to the circulating evaporator 7 is increased until the particular reflux rate of the lower alcohol that is matched to the reactants has established itself.

Then the reaction solution of the higher alcohol and the alkali alcoholate of the lower alcohol, plus additional lower alcohol as required, preheated to just below its boiling point, is delivered through line 1 continuously to the upper end of the reaction section 5. Here the solution encounters a mixture flowing down out of the booster section 2 of the column 14, whose rate of flow depends upon the rate of flow of the reflux entering the top 4 of the column through line 3. The total amount then flows downwardly through the reaction section of the column 14 in which the lighter component—here the lower alcohol—evaporates and the heavier component—here the higher alcohol—condenses out of the vapor. In this manner an ever increasing excess of higher alcohol forms in the liquid phase until a steady state is reached in the column, where it is available for the shifting of the equilibrium of the reaction towards the desired alcoholate in accordance with the equation given above.

In the sump 6, the solution is concentrated by the circulating evaporator 7 to the necessary final concentration. The end product is removed through the line 8. The vapors leaving the top 4 of the column 14 through line 9 consist of the pure lower alcohol containing minute amounts of higher alcohol. They contain as heat of evaporation the thermal energy given to them by the circulating evaporator 7. The mass of the vapors corresponds to this amount of heat. They are condensed in the condenser 10 and flow to the tank 11. In accordance with the total mass balance around the column 14, the amount of lower alcohol charged through line and in part the amount of lower alcohol liberated in the reaction section 5 is carried out through line 12 in the steady state. The amount of the lower alcohol, the plus-amount, as it is called, which is then still present in the system and which collects until the steady state is reached, can be controlled by the heating power of the evaporator 7, and it is fed into the top 4 of column 14 as reflux by means of the pump 13 through the line 3.

The output of the lower alcohol can be used without further distillative purification for the preparation of alkali alcoholates of methanol or ethanol, for example.

By the method of the invention, one can achieve a virtually quantitative reaction of the alkali alcoholate of the lower alcohol with the higher alcohol. As products, alkali alcoholates of the higher alcohol dissolved in the same higher alcohol are obtained. Since virtually no higher alcohol is removed and lost at the top of the amplifying section, the molar concentration of the final solution will be the molar concentration of the starting solution with allowance for the transalcoholization alcohol that has been consumed in the chemical reaction.

According to the solubility characteristics of the starting alcoholates and final alcoholates or according to the desired concentration of the final alcoholates in the higher alcohols, those starting alcoholate solutions are put in which contain the transalcoholization alcohol in an excess with respect to the starting alcoholate.

The desired alcoholate can be obtained in solid form in a known manner, e.g., by the evaporation of the higher alcohol.

The process is performed such that in the whole column a temperature profile of between the boiling point of the transalcoholization alcohol (in the sump) and the boiling point of the lower alcohol to be removed (at the top of the column), depending upon the pressure at the sump respectively at the top is maintained. Other than with the distillation technique the process according to the invention provides that by addition of more heat per time unit an increased reflux is produced in the sump.

The process is generally conducted at atmospheric pressure but sub- and superatomospheric pressure can also be used. Generally, the pressure can be in the range of 1 torr up to 10 bars.

The equivalence ratio of transalcoholization alcohol to alkali metal alcoholate of the lower alcohol can vary widely depending upon the amount of transalcoholization alcohol which is to be in admixture with the final product. Generally, this mole ratio is greater than 1:1, preferably so great that the reaction mixture in each point of the column is not solid.

EXAMPLE 1

A preheated solution of 3120 g of isopropanol (52 moles) and a 30% sodium methylate solution consisting of 495 g of methanol (15.5 moles) and 212 g of sodium methylate (4 moles) was fed per hour through line 1 into the reaction section, at standard pressure.

The heat input of the circulating evaporator 7 disposed adjacent the sump 6 was made such that the amount of lower alcohol returned to the top 4 through line 3 established itself at 3380 grams per hour. In steady-state operation, a reflux rate of 26 moles of methanol per mole of constantly fed sodium methylate resulted. An approximately 10 wt.-% sodium isopropylate solution was continuously withdrawn from the bottom at a rate of 3207 g of isopropanol (53.4 moles) and 321 g of sodium isopropylate (4 moles) per hour. The sodium methylate transformation amounted to 99%.

EXAMPLE 2

Similarly to Example 1, a preheated solution consisting of (a) a 30% sodium methylate solution containing 700 grams of methanol (21.8 moles) and 300 g of sodium methylate (5.5 moles) and (b) 2140 grams (35.6 moles) of isopropanol, was delivered per hour to the reaction section. The heat input was adjusted so that a reflux of 3170 grams per hour of the lower alcohol established itself. This resulted in a reflux rate of 18 moles of methanol per mole of continuously fed sodium methylate. At the top, 875 g of methanol (27.3 moles) was withdrawn with a purity of 99.9 wt.-%. From the bottom, a 20 wt.-% sodium isopropylate solution was taken at the rate of 452 g (5.5 moles) of sodium isopropylate and 1809 g (30.1 moles) of isopropanol per hour. The sodium methylate transformation was 99%.

EXAMPLE 3

The procedure was the same as in Example 1, except that 2586 g of n-butanol (34.9 moles), a 12% methanolic sodium methylate solution containing 150 g of sodium methylate (2.8 moles), and 1097 g of methanol were fed per hour into the column. The methanol reflux rate was adjusted so as to produce a molar ratio of sodium methylate to methanol of 1:6. From the top, 1185 g of methanol (37.0 moles) was withdrawn hourly with a purity of 99.98% by weight. From the bottom, a 10% sodium butylate solution was withdrawn continuously at the rate of 265 g of sodium butylate solution (2.8 moles) and 2382 g of n-butanol (32.1 moles) per hour.

EXAMPLE 4

The process of Example 1 was followed, except that the column was operated with 3269 g of tertiary butanol (44.1 mole) and a 25% methanolic solution of potassium methylate containing 237 g of potassium methylate (3.4 moles) and 675 g of methanol (21.1 mole) per hour. The heat input was adjusted such that a molar ratio of input potassium methylate to the refluxed methanol became 1:30. At the bottom of the column, an 11 wt.-% solution of potassium tertiary butanol was continuously withdrawn at the rate of 374 g of potassium tertiary butylate (3.33 moles) and 3022 g of tertiary butanol (40.77 moles) per hour.

The potassium methylate transformation amounted to 99%. The methanol withdrawn at the top had a purity of 99.99 wt.-%.

What is claimed is:

1. A process for the continuous production of an alkali metal alcoholate of a higher alcohol which comprises continuously introducing an excess of a higher alcohol selected from the group consisting of ethanol, n-propanol, n-butanol, 2-methylpropanol-(1), n-pentanol, 2-methylbutanol-(4), 2-methylbutanol-(1), 2,2-dimethylpropanol-(1), n-hexanol, 2-ethylhexanol-(1), isopropanol, butanol-(2), pentanol-(2), pentanol-(3), 2-methylbutanol-(3), 2-methylpropanol-(2), 2-methylbutanol-(2), cyclopropanol, cyclobutanol, cyclopentanol and cyclohexanol into a reaction vessel provided with different reaction zones, superposed with at least one rectification zone, continuously introducing an alkali metal alcoholate of a lower alcohol selected from the group consisting of methanol and ethanol into said reaction vessel and continuously and simultaneously distilling over and removing from said said reaction vessel a composition which is substantially pure lower alcohol and removing from said reaction vessel a solution of alkali metal alcoholate of higher alcohol in the higher alcohol and constantly adding lower alcohol to said rectification zone, the reflux rate of the lower alcohol amounting in the rectification zone from 6 to up to 200 mols per mol of alkali metal alcoholate of lower alcohol introduced into said reaction vessel provided that when the lower alcohol is ethanol, the higher alcohol is not ethanol.

2. A process according to claim 1 wherein the reaction is performed in the presence of excess higher alcohol by refluxing a part of said formed lower alcohol to the reaction vessel.

3. A process according to claim 1 wherein said higher alcohol is a primary alcohol and said reflux rate amounts up to 40 moles per mole of alkali metal alcoholate of lower alcohol.

4. A process according to claim 1 wherein said higher alcohol is a primary alcohol and said reflux rate amounts up to 12 moles per mole of alkali metal alcoholate of lower alcohol.

5. A process according to claim 1 wherein said higher alcohol is a secondary alcohol and said reflux rate amounts up to 120 moles per mole of alkali metal alcoholate of lower alcohol.

6. A process according to claim 1 wherein said higher alcohol is a secondary alcohol and said reflux rate amounts up to 50 moles per mole of alkali metal alcoholate of lower alcohol.

7. A process according to claim 1 wherein said higher alcohol is a tertiary alcohol and said reflux rate amounts up to 200 moles per mole of alkali metal alcoholate of lower alcohol.

8. A process according to claim 1 wherein said high alcohol is a tertiary alcohol and said reflux rate amounts up to 80 moles per mole of alkali metal alcoholate of lower alcohol.

9. A process according to claim 1 wherein said apparatus is in the form of a vertical column.

10. A process according to claim 1 wherein the reaction vessel contains trays or packings.

11. A process according to claim 1 wherein during said process lower alcohol is introducing into the reaction vessel.

12. A process according to claim 1 wherein the process is carried out by initially charging into the reaction vessel lower alcohol, adjusting the temperature of the same to at least the boiling point thereof, thereafter introducing alkali metal alcohol of lower alcohol together with higher alcohol withdrawing lower alcohol distillatively, condensing the same recycling a portion of the condensed lower alcohol and continuously withdrawing alkali metal alcoholate of higher alcohol together with higher alcohol from the bottom of the reaction vessel.

13. A process according to claim 1, wherein while said lower alcohol is continuously and simultaneously distilled over, higher alcohol present in the reaction mixture which is in vaporous form is condensed and returned to said reaction vessel.

14. A process according to claim 13, wherein lower alcohol which is distilled off is, prior to being distilled off, in admixture with said higher alcohol and the admixture is refluxed such that said higher alcohol is condensed and returned to said reaction vessel and said lower alcohol is distilled off.

15. A process according to claim 1, wherein only lower alcohol is continuously and simultaneously distilled over to leave behind higher alcohol.

16. A process according to claim 13, wherein only lower alcohol is continuously and simultaneously distilled over to leave behind higher alcohol.

17. A process according to claim 1, wherein said alcohol metal alcoholate of a lower alcohol is introduced into said reaction vessel in the form of a solution in lower alcohol.

* * * * *